US012122737B2

(12) United States Patent
Reimer et al.

(10) Patent No.: US 12,122,737 B2
(45) Date of Patent: Oct. 22, 2024

(54) METHOD FOR CONTINUOUSLY PRODUCING DIOLS FROM ALDEHYDES BY MEANS OF RANEY COBALT CATALYSIS

(71) Applicant: OQ Chemicals GmbH, Monheim am Rhein (DE)

(72) Inventors: Joachim Reimer, Mannheim (DE); Kurt Schalapski, Oberhausen (DE); Jan Henry Rahe, Herten (DE); Jörg Arnold, Dinslaken (DE); Marcel Musenbrock, Düsseldorf (DE)

(73) Assignee: OQ Chemicals GmbH (DE)

( * ) Notice: Subject to any disclaimer, the term of this patent is extended or adjusted under 35 U.S.C. 154(b) by 417 days.

(21) Appl. No.: 17/611,388

(22) PCT Filed: Jun. 2, 2020

(86) PCT No.: PCT/EP2020/065182
§ 371 (c)(1),
(2) Date: Nov. 15, 2021

(87) PCT Pub. No.: WO2020/245101
PCT Pub. Date: Dec. 10, 2020

(65) Prior Publication Data
US 2022/0213012 A1 Jul. 7, 2022

(30) Foreign Application Priority Data
Jun. 4, 2019 (EP) .................................... 19178117

(51) Int. Cl.
*C07C 29/141* (2006.01)
*B01J 8/02* (2006.01)
*B01J 25/00* (2006.01)
*B01J 25/02* (2006.01)
*C07C 45/75* (2006.01)

(52) U.S. Cl.
CPC .............. *C07C 29/141* (2013.01); *B01J 8/02* (2013.01); *B01J 25/00* (2013.01); *B01J 25/02* (2013.01); *C07C 45/75* (2013.01)

(58) Field of Classification Search
CPC ................................................. C07C 29/141
See application file for complete search history.

(56) References Cited

U.S. PATENT DOCUMENTS

| 3,808,280 | A | 4/1974 | Merger et al. |
| 5,922,921 | A | 7/1999 | Unruh et al. |
| 8,211,353 | B2 | 7/2012 | Dee et al. |
| 8,394,998 | B2 | 3/2013 | Schalapski et al. |
| 10,336,672 | B2 * | 7/2019 | O'Young ................ C07C 45/75 |
| 2009/0054702 | A1 | 2/2009 | Powell |
| 2011/0098515 | A1 | 4/2011 | Schalapski et al. |

FOREIGN PATENT DOCUMENTS

| CN | 102083776 A | 1/2011 |
| CN | 105008317 A | 10/2015 |
| DE | 1804984 A1 | 5/1969 |
| GB | 1219162 A | 1/1971 |
| GB | 1219162 | 6/1971 |
| JP | 51-1686 B1 | 1/1976 |
| JP | 2001521014 A | 11/2001 |
| JP | 2011526261 A | 10/2011 |
| KR | 10-2015-0076177 A | 7/2015 |
| KR | 101582107 B1 | 1/2016 |
| WO | 2008151102 A2 | 12/2008 |
| WO | 2010000382 A2 | 1/2010 |
| WO | 2014120481 A1 | 8/2014 |

OTHER PUBLICATIONS

International Preliminary Report on Patentabiity dated Dec. 7, 2021.
Written Opinion dated Jul. 29, 20.
International Search Report dated Jul. 29, 20.

* cited by examiner

*Primary Examiner* — Medhanit W Bahta
(74) *Attorney, Agent, or Firm* — M. Susan Spiering; Ochoa & Associates, P. C.

(57) ABSTRACT

The present invention relates to a process for continuous production of C4-C10 Diols from C3-C9 aldehydes comprising the process steps of: a) base-catalyzed addition of formaldehyde onto C3-C9 aldehydes to obtain the corresponding hydroxyaldehydes and b) subsequent hydrogenation of the hydroxyaldehydes to afford the corresponding diols, wherein the hydrogenation of the hydroxyaldehydes is performed continuously in the liquid phase over a Raney™ cobalt catalyst in the presence of hydrogen without workup of the reaction mixture from the process step a).

20 Claims, No Drawings

METHOD FOR CONTINUOUSLY PRODUCING DIOLS FROM ALDEHYDES BY MEANS OF RANEY COBALT CATALYSIS

CLAIM FOR PRIORITY

This application is a National Phase Application of Application no. PCT/EP2020/065182 filed Jun. 2, 2020 which was based on Application no. EP 19 178 117.8 filed Jun. 4, 2019. The priorities of the foregoing applications is hereby claimed and their disclosures incorporated herein by reference.

TECHNICAL FIELD

The present invention relates to a process for continuous production of C4-C10 Diols from C3-C9 aldehydes comprising the process steps of: a) base-catalyzed addition of formaldehyde onto C3-C9 aldehydes to obtain the corresponding hydroxyaldehydes and b) subsequent hydrogenation of the hydroxyaldehydes to afford the corresponding diols, wherein the hydrogenation of the hydroxyaldehydes is performed continuously in the liquid phase over a Raney™ cobalt catalyst in the presence of hydrogen without workup of the reaction mixture from the process step a).

BACKGROUND

The targeted functionalization of organic molecules on a large industrial scale remains a great challenge for the chemical industry even today. The reason for this is that, in addition to the application of reaction mechanisms known per se on a large industrial scale, there are further complex dependencies on other process parameters which ultimately have a decisive influence over the economy and competitiveness of the process to be utilized. Thus, in industrial practice energetic, safety, environmental and process time aspects play a significant role in addition to fundamental parameters such as conversion and selectivity.

These cross-dependencies can have the result that very promising laboratory synthesis routes are uneconomic under continuous conditions on a large industrial scale and alternative solutions represent a better choice despite boundary conditions which are a priori less advantageous.

Polyhydric alcohols or polyols are of considerable economic importance as condensation components for the synthesis of polyesters or polyurethanes, synthetic resin paints and varnishes, lubricants and plasticizers. An important representative of this class is neopentyl glycol (NPG, 2,2-dimethylpropane-(1,3)-diol) which is obtainable on a large industrial scale by a mixed aldol addition between formaldehyde and isobutanal. The aldol addition initially forms a hydroxyaldehyde which is typically isolated and must be reduced to the polyhydric alcohol in a separate process step.

For the conversion of aldehydes into alcohols the scientific and patent literature discloses a multiplicity of processes which propose a metal-catalyzed conversion in the presence of hydrogen. However, other than the commonality of the conversion of the specific functional groups, the processes vary considerably. One accordingly finds batch vs. continuous process regimes, gas-vs liquid-phase reactions, hydrogenation of the isolated aldehydes or conversion in a more complex reaction environment in the presence of further substances. These differences in the processes have had the result that as a function of the specific process mode different large industrial scale boundary conditions have proven advantageous in each case.

Thus for example WO 2014/067602 A1 describes a continuous process for producing neopentyl glycol by addition of isobutanal and formaldehyde in the presence of a tertiary alkylamine as catalyst to afford hydroxypivalaldehyde with subsequent gas-phase hydrogenation over a barium- and manganese-doped copper chromite catalyst at a temperature of 125° C. to 180° C. and at a positive pressure of 30 to 120 kPa.

Another liquid-phase option is disclosed for example by WO 2014/067600 A1. This patent document describes a process for producing neopentyl glycol by addition of isobutanal and formaldehyde in the presence of a tertiary alkylamine as catalyst to afford hydroxypivalaldehyde with subsequent liquid-phase hydrogenation over a barium- and manganese-doped copper chromite catalyst at a temperature of 80° C. to 220° C. and at a pressure of 2 to 18 MPa.

Another liquid-phase route is disclosed for example in WO 2010/000382 A1; which relates to a process for producing neopentyl glycol by addition of isobutanal and formaldehyde in the presence of a tertiary alkylamine as catalyst to afford hydroxypivalaldehyde with subsequent liquid-phase hydrogenation over a nickel catalyst at a temperature of 80° C. to 180° C. and at a pressure of 6 to 18 MPa in the presence of an aliphatic alcohol and in the presence of water.

A further process variant to obtain alcohols is reported in WO 95/32171. This document discloses a process for producing alcohols through catalytic hydrogenation of the corresponding carbonyl compounds at elevated temperature and at elevated pressure in the liquid phase, using a catalyst containing copper on an $SiO_2$-containing support material in the presence or absence of one or more of the elements magnesium, barium, zinc or chromium.

Despite the already known processes for producing alcohols from aldehydes, there remains an elevated interest in industrial processes which are capable of converting even complex reaction mixtures very efficiently and with high throughputs.

SUMMARY OF INVENTION

The present invention accordingly has for its object to provide an integral process which at least partially overcomes the disadvantages of the known processes and allows continuous conversion of aldehydes into hydroxyaldehydes and, without workup of this reaction solution, subsequent hydrogenation of the hydroxyaldehyde into the corresponding diols.

According to the invention a process for 2-stage synthesis of diols according to claim 1 is therefore proposed. Advantageous developments of the process are specified in the subsidiary claims. They may be combined as desired provided the opposite is not clearly apparent from the context.

According to the invention the process for continuous production of C4-C10 diols from C3-C9 aldehydes comprises the process steps of:
a. base-catalyzed addition of formaldehyde onto C3-C9 aldehydes to obtain the corresponding hydroxyaldehydes and
b. subsequent hydrogenation of the hydroxyaldehydes to afford the corresponding diols, wherein the hydrogenation of the hydroxyaldehydes is performed continuously in the liquid phase over a Raney cobalt catalyst in the presence of hydrogen without workup of the reaction mixture from the process step a).

It has now been found that the above process regime based on a hydrogenation step in a complex reaction environment under Raney™ cobalt catalysis exhibit several unexpected advantages for the reaction mixture and thus for the entire synthetic route. Some of the advantages are as follows:

The hydroxyaldehydes may be converted in the complex reaction mixture of the aldolization, thus allowing omission of a complex and energy intensive workup of the reaction mixture before the hydrogenation.

Stable process conditions with high conversions and selectivities are achievable for both reaction steps over wide process parameter ranges.

High conversions and selectivities are achieved even under high catalyst loadings.

The catalyst exhibits exceptional stability in the reaction environment and in particular does not have a propensity for mechanical or chemical decomposition. This guarantees long lifetimes and avoids/improves a costly and complex removal of the metals from the product.

The content of undesired byproducts from the aldolization, for example formic acid or adducts thereof, in the reaction mixture of the process step b) can be reduced.

Only a slight decomposition of the bases of the reaction step a) (for example tri-n-propylamine (TPA)) takes place in the hydrogenation, thus resulting in fewer disruptive byproducts in the product and altogether improving the recycling of the amine in process step a).

The hydrogenation is highly efficient and may even be run in a low temperature range which altogether reduces the formation of undesired byproducts.

The combination of the process steps recited hereinabove under the specified process conditions thus not only results in a high conversion, a high selectivity and a high energy efficiency but also ensures that the process may be operated stably over a long period without elevated maintenance costs. These advantages altogether result in a highly economic and environmentally friendly process.

DETAILED DESCRIPTION

The process according to the invention is a process for continuous production of C4-C10 diols from C3-C9 aldehydes. Continuous production is to be understood as meaning process regimes in which as a function of time reactants are added to the reaction site not only once but rather either continuously or else frequently over short time intervals. The same applies to the products which are withdrawn from the reaction site not altogether after a predetermined time period but rather at regular time intervals or continuously.

C3-C9 aldehydes serve as reactants for the process. Suitable input aldehydes include aliphatic and aromatic hydrocarbons having 3 to 9 carbon atoms and an aldehyde group (R—CHO). Possible input aldehydes may for example be selected from the group of aliphatic aldehydes such as propanal, butanals, pentanals, hexanals, heptanals, octanals and nonanals. Particularly this group of rather low molecular weight aldehydes shows consistently good properties in the the conversion according to the invention.

The aldehydes employable according to the invention are converted into the corresponding C4-C10 diols. This means that the conversions according to the invention lengthen the carbon backbone of the input aldehyde by at least one carbon atom, a further hydroxyl group is introduced into the reactant and the existing aldehyde group is converted into a hydroxyl group. Diols preferably obtainable by the process are for example neopentyl glycol, trimethylolpropane and higher homologues.

In a first process step a) the process comprises the base-catalyzed addition of formaldehyde onto C3-C9 aldehydes to obtain the corresponding hydroxyaldehydes. The following reaction scheme illustrates the principle conversion in the process step a) with reference to a conversion of isobutanal:

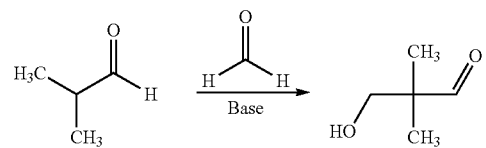

The conversion in this step affords hydroxypivalaldehyde as an intermediate. Suitable bases generally include both inorganic and organic bases. Preferred inorganic bases are for example the hydroxides of alkali metals and alkaline earth metals. Employable organic bases include tertiary alkylamines having two or more trialkylamine functions. This step is operated for example in the presence of trimethyl-, triethyl-, tri-n-propyl-, tri-isopropyl-, methyldiethyl- or methyldiisopropylamine, tri-n-butylamine, dimethyl-tert-butylamine or N,N'-tetramethylethylenediamine.

The aldehydes may be reacted with formaldehyde in a molar ratio in the process step a) but it is also possible to employ one of the two reaction partners in excess. Formaldehyde may be employed as an aqueous solution. The formaldehyde content may typically be 20% to 50% by weight. It has been found that the catalyst used in the process according to the invention has a surprisingly high resistance to formaldehyde. Molar ratios of formaldehyde to aldehyde of 1:1, generally up to 1.2:1, preferably up to 1.1:1, may therefore be established in the aldol addition stage.

The reaction between aldehyde and formaldehyde may be carried out at temperatures between 20° C. and 110° C. It is advantageously operated at 80° C. to 95° C. The reaction is generally performed at standard pressure but elevated pressure may also be employed. The base used as a catalyst may be present in the reaction mixture in an amount of 1 to 20, preferably 2 to 12, mol % based on the aldehyde.

In addition to the water from the aqueous formaldehyde solution and small amounts of methanol which may likewise be present in the aqueous formaldehyde solution, isobutanol is optionally added to the reaction mixture as a diluent. Isobutanol addition is not mandatory but if isobutanol is added the content thereof in the reaction mixture is in the range from 15% to 30% by weight, preferably 15% to 25% by weight, based on the organic proportion in the overall reaction mixture. Further solvents and diluents are not required.

The practical performance of the addition reaction is for example effected in a stirred tank, in a stirred tank cascade or in a reaction tube which may be provided with random packings or other internals for better mixing of the reactants. The conversion is exothermic and may be accelerated by heating.

The crude mixture obtained after the aldol addition is subjected to catalytic hydrogenation in the presence of the Raney™ cobalt catalyst without preceding separation into its constituents or removal of individual components.

Process step b) comprises hydrogenation of the hydroxyaldehydes to afford the corresponding diols. To continue the exemplary conversion shown in process step a), the process step b) comprises for example the following conversion:

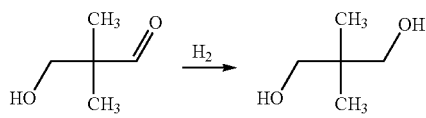

This conversion affords neopentyl glycol as the reaction product which can be isolated from the complex reaction mixture through customary purification steps and processes. Further preferably producible diols are for example neopentyl glycol, trimethylolpropane or higher homologues.

Hydrogenation of the hydroxyaldehydes in the process step b) is carried out without workup of the reaction mixture from the process step a). This means that the hydrogenation is performed on substantially the same reaction mixture as was obtained from the process step a). Such a conversion is not performed on substantially the same reaction mixture, and thus not without workup, in cases where one or more components are completely or partially intentionally withdrawn from the reaction solution through further processing operations. This may be carried out for example through customary chemical separating operations such as a distillation. A reaction solution is employed without workup for example when the concentrations of the components present therein vary by less than 5 mol %, preferably less than 2.5 mol %, more preferably less than 1.5 mol %, per component between the end of the process step a) and the start of the process step b). A reaction solution is employed substantially without workup when any concentration changes in the solution take place without deliberate external intervention, for example through a pressure or temperature change.

The process step b), i.e. the hydrogenation, is carried out continuously in the liquid phase, for example over fixed catalysts in a downflow or upflow mode or by suspension hydrogenation. This means especially that the hydrogenation is not carried out in the context of a purely gas-phase reaction. The conversion of the aldehyde group into the alcohol group may be effected for example through the use of gaseous hydrogen which is passed through the reaction mixture of the further reactant(s) which is liquid under the reaction conditions. The hydrogenation is carried out with continuous supplying of at least one reactant and continuous removal of at least one product from the reaction space.

The hydrogenation is preferably carried out in the presence of an aliphatic alcohol miscible with the aldolization product. Aliphatic alcohols which have proven suitable include linear or branched alcohols having 1 to 5 carbon atoms, for example methanol, ethanol, n-propanol, isopropanol, n-butanol, isobutanol, neopentyl glycol or mixtures thereof. It is particularly advantageous to use isobutanol since residual amounts of isobutanal are hydrogenated to afford isobutanol. If isobutanol is already employed as a diluent in the aldol addition stage a solvent is already present in the hydrogenation stage. Small amounts of methanol introduced via the aqueous formaldehyde solution are likewise present. In this embodiment of the invention the proportion of the aliphatic alcohol as organic solvent or diluent may be 15% to 27% by weight, preferably 15% to 23% by weight, based on the organic proportion in the input mixture The addition of the diluent or solvent ensures preferential solubility of the hydroxypivalaldehyde in the liquid phase during the hydrogenation stage, prevents precipitation of hydroxypivalaldehyde and ensures the homogeneity of the liquid phase. Excessive alcohol contents result in unnecessary occupation of the reactor volume.

According to the invention the process step b) is performed over a Raney™ cobalt catalyst. Raney™ cobalt catalysts are typically produced by treating a metal alloy powder with an alkali, wherein the composition of the metal alloy, based on weight, comprises about 20% to 60% of cobalt and optionally further metals such as iron, nickel, chromium, rhodium, ruthenium, osmium, iridium, platinum, palladium and mixtures of the metals of this group. The remainder of the alloy composition is a metal soluble in alkali. The alkali-soluble metals include aluminum, zinc, magnesium and silicon. Aluminum is the preferred alkali-soluble metal. The alloy from which the catalyst is produced may be produced by customary metallurgical processes for producing alloy ingots. To obtain the alloy in the desired powder form the ingot is comminuted and ground. The alloy powder is converted into the active catalyst by treatment with an aqueous alkaline solution, preferably sodium hydroxide. This solution washes out the majority of the aluminum or other alkali-soluble metal to afford the active Raney™ metal catalyst. The cobalt content of the active catalysts based on dry weight may be about 25% to about 80%. The remainder of the catalyst composition is a function of the presence of further metals as promoters and the thoroughness of the washing out process. A small amount of the alkali-soluble metal, for example aluminum, generally also remains in the catalyst. The alkali-soluble metal residues may be in the form of oxides.

The cobalt hydrogenation catalyst may very generally comprise, in addition to the catalytically active main metal, dopant metals selected from the elements of groups Ib, IIb, IVb, VIb, VIIb and VIII of the periodic table as well as aluminum which is especially present in the Raney™ metals.

The hydrogenation of the crude hydroxypivalaldehyde may be performed in the liquid phase in the presence of Raney™ cobalt catalysts at a temperature of 60° C. to 220° C., preferably of 60° C. to 180° C. and in particular of 70° C. to 160° C. Temperatures of 60-140° C. may be preferred since the temperature of the reaction mixture from the process step a) may likewise preferably be in this temperature range. The latter makes it possible to avoid costly and complex further temperature control means between the process steps. The reaction pressure is preferably 2 to 150 MPa, more preferably 60 to 120 MPa. A reaction temperature of 70° C. to 160° C. and a reaction pressure of 60 to 120 MPa have proven particularly advantageous. At lower reaction pressures adequate hydrogenation of hydroxypivalaldehyde for example is no longer observed In the continuous fixed bed mode a catalyst loading V/Vh, expressed as throughput volume per catalyst volume and time, of 0.2 to 4.0 h$^{-1}$, preferably 0.3 to 1.5 h$^{-1}$, has proven advantageous.

Hydrogenation is preferably carried out continuously in the liquid phase in a tubular reactor over fixed catalysts. A tubular reactor is also to be understood as meaning a bundle of two or more tightly packed parallel tubes. The employed tubular reactors may likewise contain random packings or internals, for example Raschig rings, saddles, Pall rings, filter plates or column trays and optionally stirring apparatuses or apparatuses for removing the reaction heat. In a particularly preferred embodiment the hydrogenation of hydroxypivalaldehyde is carried out in a tubular reactor over a fixed bed but without internals and without stirring apparatuses.

In a preferred embodiment of the process the Raney cobalt catalyst may be in the form of a fixed bed. A fixed bed reactors is understood as meaning a reactor form in which one or more fluids and/or gases flow through a solid dumped bed or packing. Especially the use of the catalyst as a fixed bed has proven particularly advantageous in the process according to the invention. The fixed dumped bed prevents excessive mechanical stress on the individual catalyst particles and can contribute to a greater hydrogen exchange area. This can contribute to higher conversions and to a lower contamination of the end product with undesired metal traces.

The process step b), the hydrogenation, is performed in the presence of hydrogen. The hydrogenation is preferably carried out with pure hydrogen. However, it is also possible to employ mixtures containing free hydrogen and also constituents that are inert under the hydrogenation conditions. The hydrogenation is advantageously performed by subjecting the reaction vessel to hydrogen pressure, wherein the hydrogen pressure may generally be between 0.1 and 200 MPa. The hydrogen gas may be applied to or introduced into the reactor using technical measures known to those skilled in the art and it may be advantageous for the hydrogen to be passed through the liquid reaction mixture.

In a further embodiment of the process isobutanal may be reacted with aqueous formaldehyde solution to afford hydroxypivalaldehyde in the process step a) and the hydroxypivalaldehyde may be hydrogenated to afford neopentyl glycol in the process step b). It has surprisingly been found that the process according to the invention especially allows particularly efficient accomplishment of the the abovementioned conversions utilizing a Raney™ cobalt catalyst. High conversions and high selectivities are achievable even at very high throughputs and, though without wishing to be bound to theory, this is thought to be partly due to a preferred alignment of the reactants on the Raney™ cobalt catalyst and to the chemical reaction environment of the process step a).

In a preferred process variant the base in the process step a) may be selected from the group consisting of trimethylamine, triethylamine, tri-n-propylamine or tri-n-butylamine or mixtures of at least two constituents thereof. The use of organic bases as catalyst in particular does not only contribute to the achievement of a very effective first process step a). It has also proven advantageous for the process step b) when said step is performed over a Raney™ cobalt catalyst in the presence of the abovementioned tertiary amines. These bases do not have a negative impact on hydrogenation and neither are they converted in appreciable yield by the chosen catalyst system, thus allowing them to be recycled back into the process step a) after workup.

Another advantage is that in case of thermal removal of the base the energy input would lead to an increased formation of high boilers (especially hydroxypivalic acid neopentyl glycol ester, HPN) which under the mild hydrogenation conditions can be cleaved back into value product only to a limited extent.

In a further embodiment of the process the Raney™ cobalt catalyst may comprise further metals selected from the group consisting of chromium, molybdenum, iron, nickel, copper, ruthenium, palladium, platinum, manganese, rhodium or mixtures of at least two constituents thereof. In addition to conversion over a pure Raney™ cobalt catalyst it has proven advantageous in terms of conversion and process stability for further metals to be present in the catalyst in addition to the Raney™ alloy having cobalt as a constituent. This can extend the lifetime of the catalyst and allow stable process management over a wide process parameter range.

In a preferred embodiment of the process the Raney cobalt catalyst may contain not only cobalt but also the metals chromium and nickel in a weight fraction of not less than 0.05% and not more than 10%. In the context of a continuous process the addition of chromium and nickel in particular can contribute to efficient running even at relatively high catalyst loadings. Relatively large reactant quantities per unit time may be converted, thus enhancing the economy of the process.

In an additional process variant the hydrogenation in the process step b) may be performed at a temperature of not less than 70° C. and not more than 160° C. The selected process regime and the selected catalyst system can contribute to the achievability of stable conversions with only a small proportion of undesired byproducts over a wide temperature range. This is remarkable since this is possible even in a rather moderate or relatively low temperature range with high conversions. This accordingly results in very economic conversions which also have the feature that the cost and complexity required for purifying the end products can be kept low. The temperature in the process step b) may preferably be not less than 95° C. and not more than 145° C.

In a further preferred embodiment of the process the catalyst loading LHSV (liquid hourly space velocity) in the process step b) may be not less than 0.3 $h^{-1}$ and not more than 1.5 $h^{-1}$. Despite the presence of a very complex reaction mixture comprising components from the process step a) the catalyst system employed here make it possible to achieve high catalyst loadings, reported in the form of space velocity and defined as volume flow of reactant per volume of dumped catalyst bed, without leaving the zone of high conversions and selectivities. This is advantageous especially for continuous processes and can contribute to an improved economy and energy efficiency of the process.

In the context of a preferred embodiment of the process the concentration of the base in the process step b) may be not less than 3% by weight and not more than 15% by weight. It has been found that the Raney™ cobalt catalyst system is highly tolerant of the base employed in the process step a) so that even without preceding removal and with high base concentrations very efficient hydrogenations may be performed in the process step b). The catalyst does not undergo leaching even under the high loadings and an undesired metal content in the end product is avoided. This especially results in a more efficient overall process since the base catalyst amount employed in process step a) may be effectively decoupled from the conditions in process step b).

In a preferred embodiment of the process the molar ratio of hydrogen to hydroxyaldehyde in the process step b) may be not less than 1:1 and not more than 100:1. To obtain the highest possible space velocities the abovementioned molar hydrogen:reactant ratios have proven particularly advantageous. The kinetics provided by the Raney™ cobalt catalyst system allows for supply of relatively large hydrogen quantities and the proportion of undesired byproducts can be kept very low. Thus altogether large product quantities may be provided in very short time periods.

In a preferred embodiment of the process the pressure in the process step b) may be not less than 60 MPa and not more than 120 MPa. Despite the complex reaction mixture present in process step b) it has proven advantageous to perform the hydrogenation at relatively high pressures. This can have a positive impact on the kinetics of the hydrogenation over the Raney™ cobalt catalyst system and altogether contribute to improved plant utilization. Particularly high conversions and selectivities are preferably also obtainable between not less than 80 MPa and not more than 100 MPa.

In a further preferred embodiment of the process the hydroxyaldehyde content at commencement of the process step b) may be not less than 15% by weight and not more than 85% by weight. The process according to the invention also makes it possible to produce complex product mixtures with high proportions of hydroxyaldehydes safely and while avoiding excessive byproduct proportions. The hydroxyaldehyde content may be determined for example by HPLC methods or gas chromatography. In addition, the content may preferably be not less than 25% by weight and not more than 70% by weight.

In a further alternative of the process the liquid phase in the process step b) may have a water content of not less than 5% by weight and not more than 70% by weight. The process according to the invention has proven particularly robust even towards the presence of relatively large water quantities. These water quantities thus do not result in deactivation of the Raney™ cobalt catalyst. Moreover, these water quantities can in fact contribute to making it possible to provide a smaller amount of undesired byproducts.

In a further alternative of the process the reaction solution in process step b) may comprise esters, wherein the ester content at commencement of the process step b) is not less than 0% by weight and not more than 20% by weight. A substantial advantage of the Raney™ cobalt catalyst used here is that even undesired byproducts of the first process step can be converted into the desired products again in the second process step. Accordingly the 2-stage process according to the invention is not only stable towards the presence of high byproduct quantities but it can also contribute to a marked increase in yield by specifically converting these byproducts into value products. Esters are generally organic substances comprising an ester group. These esters may include for example Tishchenko esters formed by a Tishchenko reaction of the hydroxyaldehydes with themselves or with other aldehydes. Examples of these compounds include neopentyl glycol monoisobutyrate and hydroxypivalic acid neopentyl glycol ester (HPN).

In a further preferred embodiment of the process the reaction solution in process step b) may comprise formic acid, salts thereof and/or formic acid-amine adducts, wherein the content thereof at commencement of the process step b) is not less than 0% by weight and not more than 3% by weight. It has also proven advantageous that the process regime according to the invention with the Raney™ cobalt catalyst used according to the invention is also exceptionally tolerant towards high formic acid loadings. Catalyst performance is not impaired even by high contents and it has also been found that the formic acid is converted quantitatively in the process step b) even at high catalyst loadings and at low temperatures. Especially the latter can contribute to the undesired byproduct NPG monoformate being largely avoided.

In a preferred embodiment the aldehydes may be selected from the group of C3-C7 aldehydes, more preferably from the group of C3-05 aldehydes. Particularly the aldehydes having a lower C number may be particularly efficiently converted at high reactor loadings in the context of the process according to the invention.

EXAMPLES

Methods

Concentration determinations for the organic substances such as for example HPA, NPG, NPG monoisobutyrates, the acids (hydroxypivalic acid, isobutyric acid) and the Tishchenko esters were carried out by GC-FID. Concentration determinations for formic acid were likewise carried out by GC-FID after derivatization with N,O-bis(trimethylsilyl) trifluoroacetamide (BSTFA). The method of concentration determination was performed based on DIN 51405.

Concentration determination for amine compounds, for example the TPA decomposition products, di-n-propylamine and methyl-di-n-propylamine was carried out by GC-PND based on DIN 51405 using a tributylamine internal standard.

Determination of metallic components was carried out by ICP-OES/ICP-MS based on DIN 51405.

Catalysts

For the comparative tests altogether 4 catalysts were tested. These were a Kieselguh-supported nickel catalyst having a poured density of about 0.8-1.0 g/cm$^3$ and three Raney™ catalysts having a poured density between 1.6 and 1.9 g/cm$^3$.

I. Batch Experiment

Process Step a): Production of a "Crude" HPA Mixture

The process step a) in which the base-catalyzed addition of formaldehyde onto the aldehydes to obtain the corresponding hydroxyaldehydes is performed by reaction of isobutanal with 49% aqueous formalin solution and a catalyst solution containing 30% by weight of tri-n-propylamine in isobutanol. The reaction is advantageously performed in a continuous stirred tank cascade comprising 2 stirred tanks having a volume of 0.55 litres each. The input streams are 0.448 l/h of isobutanal, 0.260 l/h of a 49% formalin solution and 0.172 l/h of catalyst solution. The temperature is −97° C. in the first reactor and 103° C. in the second reactor. The input streams are continuously conveyed using pumps. The first reactor serves especially for mixing and commencement of the reaction. In the second reactor the reaction mixture reacts further until it has achieved the desired degree of conversion.

A typical composition of a reaction mixture is as follows (reported amounts in GC-FI % (water-free) & % by weight for water):

| | |
|---|---|
| Formic acid (silylation) | 0.55 |
| Isobutyric acid (silylation) | 0.01 |
| Hydroxpivalic acid (silylation) | 0.04 |
| Isobutanal | 1.58 |
| Methanol | 0.12 |
| TPA | 8.81 |
| Isobutanol | 19.46 |
| HPA | 59.81 |
| NPG monoisobutyrate | 0.61 |
| NPG | 1.92 |
| HPN | 3.96 |
| Other secondary components | 3.73 |
| Water (Karl-Fischer titration) | ~20 |

Process Step b): Batch Hydrogenation Experiment 10 g of catalyst were filled into a stainless steel basket which was subsequently introduced into an autoclave with 600 mL of crude HPA solution obtained from the process step a) and employed without further workup. The autoclave was pressurized with 80 kPa of hydrogen gas, heated to 125° C. and allowed to react for 12 hours. The resulting reaction mixtures were analyzed by GC.

|  | NPG in GC area % |
|---|---|
| Raney™ cobalt | 25.9 |
| Raney™ copper | 26.7 |
| Raney™ nickel | 24.8 |
| Nickel | 17.8 |

The batch experiment shows that the Raney™ catalysts show a comparable quantitative activity and thus a comparable conversion of the intermediate to the desired NPG target product. Compared to a supported nickel catalyst system the reactions provide significantly higher conversions. In the batch experiments secondary component formation is very high as a result of the lengthy residence times and this is why only small amounts of NPG are obtained compared to the HPA content in the input. The values therefore only provide an initial indication.

II. Continuous Production

The continuous hydrogenations were performed using a fixed bed reactor having a 600 mL catalyst volume. The hydrogenation reactor consists of a tube having an internal diameter of 32 mm which is traversed by the reactants (reaction mixture from process step a) and hydrogen) flow from below. The tube is mantle-heated via an oil thermostat has a central multipoint thermocouple for temperature measurement. The reported temperatures in each case correspond to the temperature maximum in the temperature profile over the reactor height. The reaction mixture from process step a) is continuously supplied via a high-pressure pump. The reported catalyst loadings/throughputs (LHSV) are calculated from the employed mass flow of the reaction mixture from process step a) divided by the employed dumped bed volume of the catalyst. The hydrogen stream is measured and controlled before reactor entry via a mass meter and after a high-pressure phase separator arranged downstream of the reactor via the offgas quantity.

The composition of the reaction mixture from the process step a) corresponded on average to the "crude" composition of the batch experiment (see above). The initial charge of the reaction mixture is heated to 50° C. and stirred to prevent precipitation or heterogenization. To differentiate system performance the experiments were performed at different catalyst loadings and temperatures II.1 Mechanical Stability The different catalysts were subjected to a continuous hydrogenation over 20 days at a temperature of 135° C. as a function of LHSV.

|  | Amount of metal in product in ppm | Comment |
|---|---|---|
| Raney™ cobalt | 0.06 | — |
| Raney™ copper | 0.12 | catalyst particles dissolve poor mechanical stability |
| Raney™ nickel | 0.01 | — |
| Nickel | 6-7 (silicon) | Support dissolves |

II.2 LHSV Dependence

The dependence of selectivity and conversion were monitored over 5 days in each case at T=135° C. and different throughputs (LHSV 0.35 and 1.00 h$^{-1}$). The average of five individual measurements is reported. The following results were obtained.

| Conversion in % at | LHSV = 0.35 h$^{-1}$ | LHSV = 1.00 h$^{-1}$ |
|---|---|---|
| Raney™ cobalt | 100.0 | 100.0 |
| Raney™ copper | 100.0 | 99.9 |
| Raney™ nickel | 99.8 | 79.1 |
| Nickel | 100.0 | 99.5 |

| Selectivity at | LHSV = 0.35 h$^{-1}$ | LHSV = 1.00 h$^{-1}$ |
|---|---|---|
| Raney™ cobalt | 101.2* | 100.1** |
| Raney™ copper | 99.0 | 95.3 |
| Raney™ nickel | 99.4 | 61.0 |
| Nickel | 99.0 | 98.8 |

*An arithmetic selectivity of >100% is obtained by cleavage of secondary components to NPG.
**at LHSV = 1.2 h$^{-1}$ II.3 Temperature Dependence For the Raney™ cobalt catalyst and the supported nickel catalyst temperature dependence was investigated in a further test. A throughput of LHSV=0.6 h$^{-1}$ was selected here. Both catalysts show full conversion at 145° C. Marked differences are apparent at 95° C. At 99.9% the Raney™ cobalt catalyst still provides approximately complete conversion while the supported nickel catalyst provides on average 90.4% conversion.

| Conversion in % LHSV = 0.6 h$^{-1}$ | T = 95° C. | T = 145° C |
|---|---|---|
| Raney™ cobalt | 99.9 | 100.0 |
| Nickel | 90.4 | 100.0 |

II.4 Formic Acid Conversion

The conversion of formic acid was investigated at 120° C. and an LHSV of 0.4 h$^{-1}$. In an average of 54 individual measurements the supported nickel catalyst converts 91.2% of the formic acid present in the reactant. By contrast, the Raney™ cobalt catalyst converts 99.5% of the formic acid. At high temperatures and high throughputs the conversion of formic acid falls. At T=95° C. and LHSV=0.6 h$^{-1}$ the formic acid conversion for the supported nickel catalyst is 35.6% and for the Raney™ cobalt catalyst is 59.4%. High conversions of formic acid are desirable to avoid formation of NPG formates in the distillation. Compared to the supported nickel catalyst the Raney™ cobalt catalyst also makes it possible to perform the reaction at substantially higher throughputs and lower temperatures.

II.5 Conversion of NPG Isobutyrate and HPN

The conversions of the higher boilers NPG monoisobutyrate and HPN were investigated at T=145° C. and LHSV=0.35 h$^{-1}$. It was found that the Raney™ cobalt catalyst provided the best conversions. High conversions for the high boilers are advantageous since these can be cleaved into value product (NPG monoisobutyrate provides one equivalent, and HPN 2 equivalents, of NPG). The experiments were performed at T=145° C. and at an LHSV=0.35 h$^{-1}$

| Conversion in % | NPG monoisobutyrate | HPN |
|---|---|---|
| Raney™ cobalt | 21.7 | 26.0 |
| Raney™ copper | 15.89 | 17.1 |
| Raney™ nickel | 2.1 | 9.4 |
| Nickel | 18.0 | 22.0 |

II.6 Conversion of Tri-n-Propylamine

In order to investigate the different conversions of tri-n-propylamine the Raney™ cobalt catalyst was compared to the supported nickel catalyst in a test program of altogether 14 weeks in duration. Under the experimental conditions of T=120° C. and LHSV=0.4 h$^{-1}$ the average values from 54 individual measurements gave a conversion of tri-n-propylamine of 6.99% for the supported nickel catalyst and 0.19% for the Raney™ cobalt catalyst. At high temperatures and low throughputs (long residence times) the conversion of tri-n-propylamine increases. At T=145° C. and LHSV=0.2 the conversions were on average (10 individual monuments) 38.8% for the supported nickel catalyst and 12.4% for the Raney™ cobalt catalyst. Due to the lower values for the conversion the Raney™ cobalt catalyst is thus highly advantageous for a recycling of the TPA back into process step a). In addition, the TPA can form byproducts which are difficult to remove from the value product.

The invention claimed is:

1. Process for continuous production of C4-C10 diols from C3-C9 aldehydes comprising the process steps of:
   a. base-catalyzed addition of formaldehyde onto C3-C9 aldehydes to obtain the corresponding hydroxyaldehydes; and,
   b. subsequent hydrogenation of the hydroxyaldehydes to afford the corresponding diols, characterized in that the hydrogenation of the hydroxyaldehydes is performed continuously in the liquid phase over an active cobalt hydrogenation catalyst in the presence of hydrogen without workup of the reaction mixture from the process step a);
   wherein the active cobalt hydrogenation catalyst comprises an alloy composition of about 25% to about 80% cobalt, metal selected from the group consisting of iron, nickel, chromium, rhodium, ruthenium, osmium, iridium, platinum, palladium and mixtures of these metals, with the remainder of the alloy composition being an alkali-soluble metal selected from the group of aluminum, zinc, magnesium and silicon, and dopant metals selected from the elements of groups Ib, IIb, IVb, VIb, VIIb and VIII of the periodic table.

2. Process according to claim 1, wherein the cobalt hydrogenation catalyst is in the form of a fixed bed.

3. Process according to claim 1, wherein isobutanal is reacted with aqueous formaldehyde solution to afford hydroxypivalaldehyde in the process step a) and the hydroxypivalaldehyde is hydrogenated to afford neopentyl glycol in the process step b).

4. Process according to claim 1, wherein the base in the process step a) may be selected from the group consisting of trimethylamine, triethylamine, tri-n-propylamine or tri-n-butylamine or mixtures of at least two constituents thereof.

5. Process according to claim 1, wherein cobalt hydrogenation catalyst comprises further metal selected from the group consisting of, molybdenum, copper, manganese, or mixtures of at least two constituents thereof.

6. Process according to claim 1, wherein the cobalt hydrogenation catalyst contains not only cobalt but also the metals chromium and nickel in a weight fraction of not less than or equal to 0.05% and not more than or equal to 10%.

7. Process according to claim 1, wherein the hydrogenation in the process step b) is performed at a temperature of not less than or equal to 70° C. and not more than or equal to 160° C.

8. Process according to claim 1, wherein the catalyst loading LHSV (liquid hourly space velocity) in the process step b) is not less than or equal to 0.3 h$^{-1}$ and not more than or equal to 1.5 h$^{-1}$.

9. Process according claim 1, wherein the concentration of the base in the process step b) is not less than or equal to 3% by weight and not more than or equal to 15% by weight.

10. Process according to claim 1, wherein the molar ratio of hydrogen to hydroxyaldehyde in the process step b) is not less than or equal to 1:1 and not more than or equal to 100:1.

11. Process according claim 1, wherein the pressure in the process step b) is not less than or equal to 60 MPa and not more than or equal to 120 MPa.

12. Process according to claim 1, wherein the hydroxyaldehyde content at commencement of the process step b) is not less than or equal to 15% by weight and not more than or equal to 85% by weight.

13. Process according to claim 1, wherein the liquid phase in the process step b) has a water content of not less than or equal to 5% by weight and not more than or equal to 70% by weight.

14. Process according claim 1, wherein the reaction solution in process step b) comprise esters, wherein the ester content at commencement of the process step b) is greater than or equal to 0% by weight and not more than or equal to 20% by weight.

15. Process according claim 1, wherein the reaction solution in process step b) comprises formic acid, salts thereof and/or formic acid-amine adducts, wherein the content thereof at commencement of the process step b) is greater than or equal to 0% by weight and not more than or equal to 3% by weight.

16. Process according to claim 2, wherein isobutanal is reacted with aqueous formaldehyde solution to afford hydroxypivalaldehyde in the process step a) and the hydroxypivalaldehyde is hydrogenated to afford neopentyl glycol in the process step b).

17. Process according to claim 2, wherein the base in the process step a) may be selected from the group consisting of trimethylamine, triethylamine, tri-n-propylamine or tri-n-butylamine or mixtures of at least two constituents thereof.

18. Process according to claim 2, wherein the cobalt hydrogenation catalyst comprises further metal selected from the group consisting of molybdenum, copper, manganese, or mixtures thereof of at least two constituents thereof.

19. Process according to claim 2, wherein the cobalt hydrogenation catalyst contains not only cobalt but also the metals chromium and nickel in a weight fraction of not less than or equal to 0.05% and not more than or equal to 10%.

20. Process according to claim 2, wherein the hydrogenation in the process step b) is performed at a temperature of not less than or equal to 70° C. and not more than or equal to 160° C.

* * * * *